(12) United States Patent
Hogg et al.

(10) Patent No.: US 6,527,782 B2
(45) Date of Patent: Mar. 4, 2003

(54) GUIDE FOR MEDICAL DEVICES

(75) Inventors: Bevil J. Hogg, St. Louis, MO (US); Jeffrey M. Garibaldi, St. Louis, MO (US); Scott G. Klimek, Spring Lake Park, MN (US)

(73) Assignee: Sterotaxis, Inc., St. Louis, MO (US)

( * ) Notice: Subject to any disclaimer, the term of this patent is extended or adjusted under 35 U.S.C. 154(b) by 0 days.

(21) Appl. No.: 09/875,279

(22) Filed: Jun. 6, 2001

(65) Prior Publication Data

US 2002/0074005 A1 Jun. 20, 2002

Related U.S. Application Data

(60) Provisional application No. 60/210,183, filed on Jun. 7, 2000.

(51) Int. Cl.$^7$ ................................................ A61B 19/00
(52) U.S. Cl. ...................................... 606/130; 128/899
(58) Field of Search .............................. 606/53, 56, 59, 606/72, 79, 80, 87, 96, 130, 102–108; 600/426, 427, 429; 128/899

(56) References Cited

U.S. PATENT DOCUMENTS

| | | | |
|---|---|---|---|
| 5,334,207 A | 8/1994 | Gay, Jr. | |
| 5,353,807 A | 10/1994 | DeMarco | |
| 5,429,131 A | 7/1995 | Scheinman et al. | |
| 5,810,841 A * | 9/1998 | McNeiney et al. | 33/286 |
| 6,013,038 A | 1/2000 | Pflueger | |
| 6,206,890 B1 * | 3/2001 | Truwit | 600/417 |
| 6,214,019 B1 * | 4/2001 | Manwaring et al. | 606/130 |
| 6,261,300 B1 * | 7/2001 | Carol et al. | 600/417 |
| 6,267,769 B1 | 7/2001 | Truwit | |
| 6,267,770 B1 * | 7/2001 | Truwit | 600/417 |
| 6,328,748 B1 * | 12/2001 | Hennig | 606/130 |
| 6,401,723 B1 * | 6/2002 | Garibaldi et al. | 128/899 |

* cited by examiner

*Primary Examiner*—Pedro Philogene
(74) *Attorney, Agent, or Firm*—Harness, Dickey & Pierce, P.L.C.

(57) ABSTRACT

A guide for controlling the orientation of a medical device includes a cannula having a lumen therein for the medical device, and a guide member having a passage therein for receiving and directing the medical device, the guide member being movably mounted in the cannula for movement. The guide member can be magnetically responsive to an externally applied magnetic field, or can be magnetically responsive to an externally applied magnetic field when a magnetic medical device is in the passage, and/or it can be mechanically responsive.

16 Claims, 10 Drawing Sheets

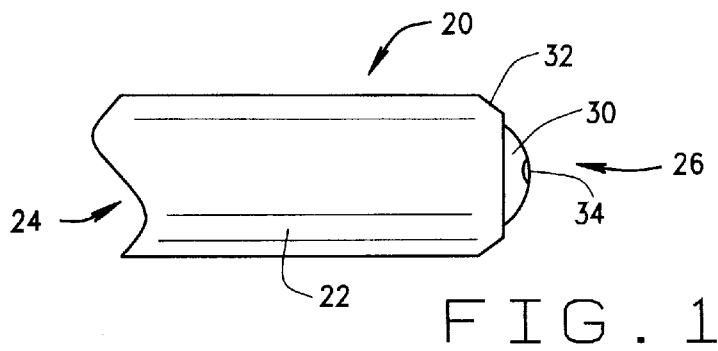
FIG. 1
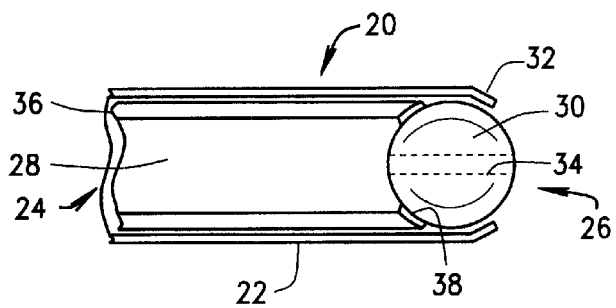 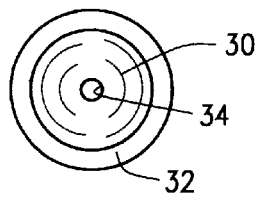
FIG. 2  FIG. 3
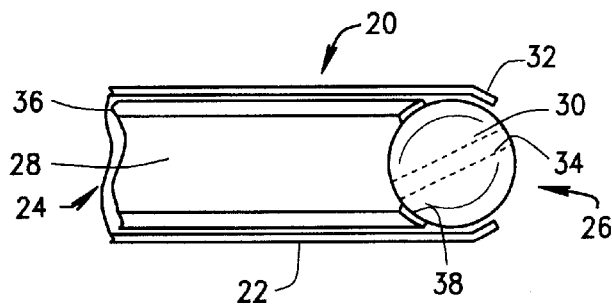 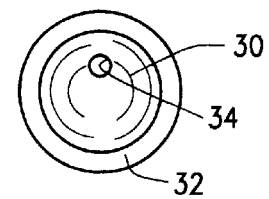
FIG. 4  FIG. 5
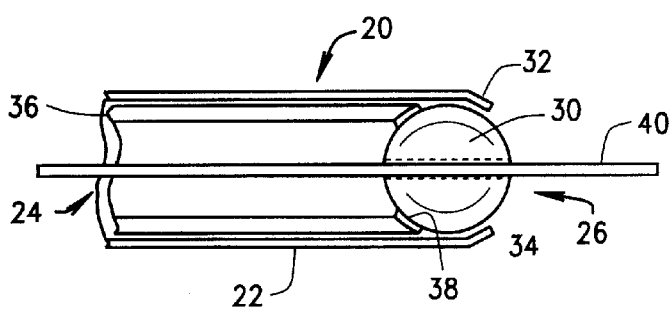
FIG. 6
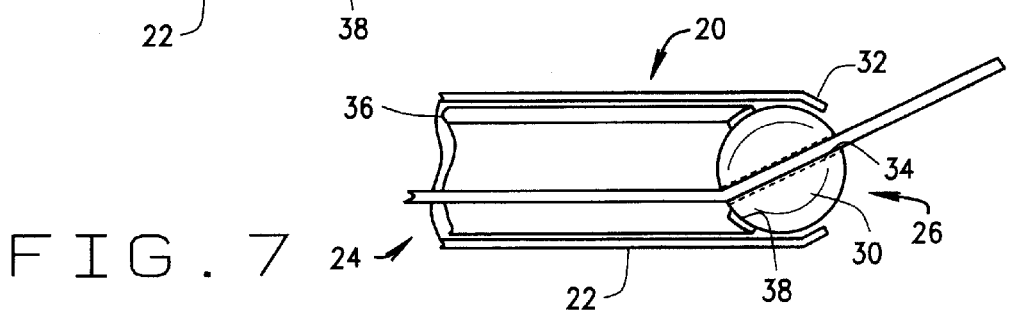
FIG. 7

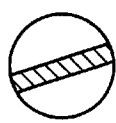
FIG.31A
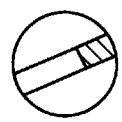
FIG.31B
FIG.31C
FIG.31D
FIG.31E
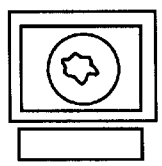
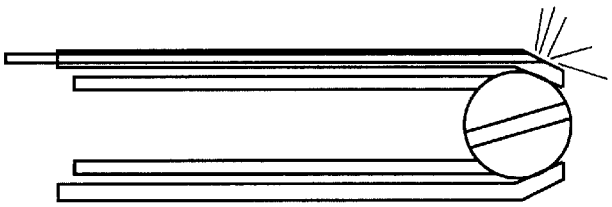
FIG.32A
FIG.32
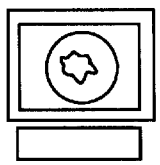
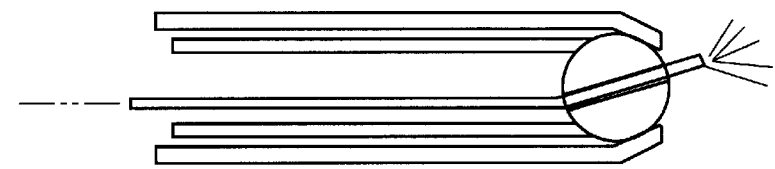
FIG.33A
FIG.33
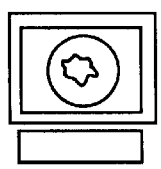
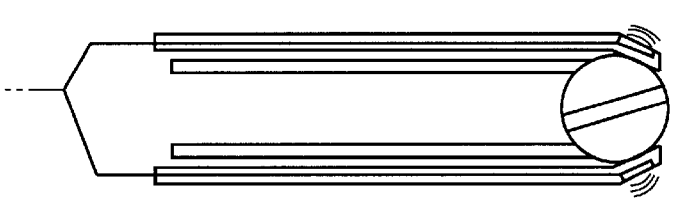
FIG.34A
FIG.34
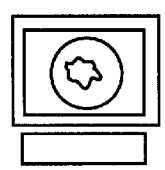
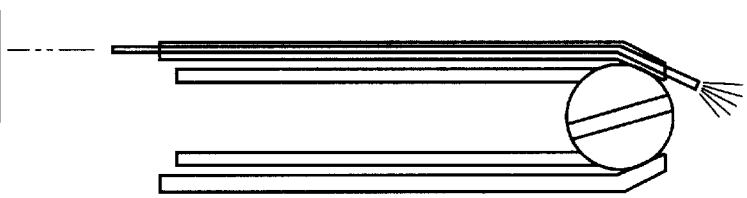
FIG.35A
FIG.35

GUIDE FOR MEDICAL DEVICES

CROSS REFERENCE TO RELATED APPLICATION

This invention claims priority from U.S. Provisional Application Serial No. 60/210,183, filed Jun. 7, 2000, for Guide for Medical Devices.

BACKGROUND OF THE INVENTION

This invention relates to medical devices, and in particular to a guide for controlling the orientation or direction of a medical device.

Control of medical devices inside the body is a persistent problem. It is important to accurately control medical devices so that they quickly and effectively perform their diagnostic or therapeutic function, while minimizing collateral damage to surrounding tissue. A particular difficulty has been selectively controlling the direction in which a medical device is deployed from a location inside the body, for example while implanting a deep brain stimulator. With the equipment and methods presently available, the placement of a device in the brain frequently involves forming a straight path to the site from a burr hole in the skull. When several devices are placed in the brain, or when a single device is placed in several locations, a number of separate paths are made from the burr hole to the separate locations. It would be preferred to have a single main path from the burr hole with a plurality of branches extending to the separate locations. However there is no device that accurately and easily guides medical devices in a plurality of separate branches. Similar problems are encountered when navigating through other body tissues.

Another difficulty with the prior art devices is the accurate navigation of medical devices in body lumens and cavities. It is often desired to deploy a medical device in a body lumen or cavity in a particular direction, or to make contact in a particular orientation, for example with the needles used in the delivery of gene therapy, particularly in the heart.

SUMMARY OF THE INVENTION

Generally, the present invention relates to a guide for deploying a medical device in the body. The guide comprises a cannula, having a proximal end, a distal end, and lumen therebetween. There is a guide member, with a passage therethrough movably mounted in the lumen of the cannula. The guide member can be magnetically or mechanically moved to change the orientation of the passage in the guide member, and thus the direction of deployment of a medical device from the guide. The guide thus allows the direction of deployment of a medical device to be precisely controlled, and further allows a medical device to be deployed in a number of separate paths from the same device. The guide also facilitates the automation of the deployment of medical devices.

The guide of this invention can also be used to orient a built-in device, such as a sensor or camera or fiber optic lead, or a therapeutic component such as a laser.

These and other features and advantages will be in part apparent and in part pointed out hereinafter.

BRIEF DESCRIPTION OF THE DRAWINGS

FIG. 1 is a side elevation view of a first embodiment of a guide for medical devices constructed according to the principles of this invention;

FIG. 2 is a longitudinal cross-sectional view of the guide of the first embodiment;

FIG. 3 is an end elevation view of the guide of the first embodiment;

FIG. 4 is a longitudinal cross sectional view of the guide of the first embodiment, with the guide member moved from its position in FIG. 2;

FIG. 5 is an end elevation view of the guide of the first embodiment as it was shown in FIG. 4;

FIG. 6 is a longitudinal cross sectional view of the guide of the first embodiment, with the guide member in a first orientation, showing a medical device extending from the guide in a first direction;

FIG. 7 is a longitudinal cross sectional view of the guide of the first embodiment, with the guide member in a second orientation, showing a medical device extending from the guide in a second direction;

FIGS. 31A–31E are plan views of radioopaque patterns that can be incorporated into the guides of the various embodiments of the redirection device of this invention, so that the position and orientation of the guide is visible in x-ray and fluoroscopic images;

FIG. 32 is a longitudinal cross sectional view of a redirection device incorporating a first distal imaging system, that can be incorporated into the various embodiments of the redirection devices of the present invention;

FIG. 32A is a representation of the distal end imaging with the first imaging system;

FIG. 33 is a longitudinal cross sectional view of a redirection device incorporating a second distal imaging system, that can be incorporated into the various embodiments of the redirection devices of the present invention;

FIG. 33A is a representation of the distal end imaging with the second imaging system;

FIG. 34 is a longitudinal cross sectional view of a redirection device incorporating a first distal imaging system, that can be incorporated into the various embodiments of the redirection devices of the present invention;

FIG. 34A is a representation of the distal end imaging;

FIG. 35 is a longitudinal cross sectional view of a redirection device incorporating a first distal imaging system, that can be incorporated into the various embodiments of the redirection devices of the present invention; and FIG. 35A is a representation of the distal end imaging.

Corresponding reference numerals indicate corresponding parts throughout the several views of the drawings.

DETAILED DESCRIPTION OF THE INVENTION

Figure 8:
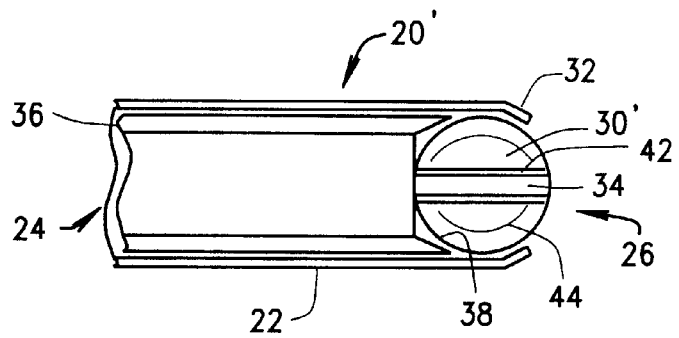
FIG. 8 is a longitudinal cross sectional view of an alternate construction of the guide of the first embodiment, in which the guide member is a composite of permanent magnetic and permeable magnetic material.

A first embodiment of a guide for a medical device constructed according to the principles of this invention is indicated generally as 20 in FIGS. 1 through 5. The guide 20 comprises a cannula 22, having a proximal end 24, and a distal end 26, and a lumen 28 therethrough. The cannula 22 is preferably fairly stiff or rigid, made from any suitable material, such as a non-magnetic stainless steel. Of course in appropriate applications, the cannula 22 could be flexible.

There is a guide member 30 in the cannula 22, mounted for movement in response to an applied magnetic field. In the first preferred embodiment shown in the Figures, the distal end 26 has a lip 32 for retaining the guide member 30 in the cannula. 'Me guide member 30 has a passage 34 therethrough for orienting or guiding a magnetic medical device.

The guide member 30 is preferably generally spherical, and the passage extends generally diametrically through the sphere. The guide member 30 is preferably made of a magnetic material so that the guide member moves in response to an externally applied magnetic field. This magnetic material may either be a permeable magnetic material, or preferably a permanent magnetic material. A permanent magnetic material allows the guide member to have a permanent magnetic orientation so that when a magnetic field is applied, the direction of the guide member is precisely controlled. When a permeable magnetic material is used, the orientation of the guide member can be ambiguous, and to prevent the guide member from assuming an undesirable orientation, stops (not shown) may be provided on the guide member. Of course, instead of, or in addition to making the guide member magnetically responsive, the distal end of the medical device can provided with a magnet, and when the magnet on the distal end of the medical device is in the passage, the magnet makes the guide member magnetically responsive.

The guide 20 preferably further comprises a lock for selectively locking the guide member 30 in a selected orientation. In this preferred embodiment the lock is a sleeve 36, with a beveled distal end 38 for engaging the guide member, that can be advanced distally to engage and lock the guide member 30, and retracted proximally to release the guide member to allow it to move in response to an applied magnetic field. The sleeve 36 is preferably biased with a spring, which mediates the force applied on the guide member preventing deformation of the guide member, and reducing the risk that the guide member will be pushed from the distal end of the guide.

As shown in FIGS. 2 and 4, when the lock is not engaged, the guide member 30 can freely move in response to an applied magnetic field from a first orientation, shown in FIGS. 2 and 3 to a second orientation as shown in FIGS. 4 and 5. As illustrated in FIGS. 6 and 7, this allows the direction of deployment of a medical device to be selectively controlled. When a medical device 40 is advanced through the guide, it passes through the lumen 28 in the cannula 22, and into the passage 34 in the guide member 30. The medical device 40 thus exits the guide 20 in a selected direction depending on the orientation of the guide member 30. Thus, when the guide member is in a first position or orientation as shown in FIGS. 2 and 3, it directs the medical device 40 in a first direction or orientation as shown in FIG. 6, and when the guide member is in a second position or orientation as shown in FIGS. 4 and 5, it directs the medical device 40 in a second direction or orientation as shown in FIG. 7.

The orientation and deployment of the medical device 40 can be easily controlled. Once a desired direction is determined, one or more externally electromagnets can be energized and/or positioned to provide the necessary magnetic field to orient the guide member 30 in the direction necessary to achieve the desired direction of the medical device, and/or one or more permanent magnets can positioned and/or oriented to provide the necessary magnetic field to orient the guide member 30 in the direction necessary to achieve the desired direction of the medical device. The orientation and deployment of the medical device can even be automated, for example using a computer interface that allows the user to select a desired direction or even a desired destination for the deployment of the medical device. A computer can then determine the magnetic field necessary to properly orient the guide member to achieve the desired direction or the desired destination point or points, or volume or surface of points, and operate one or more electromagnets and/or one or more permanent magnets to achieve the necessary magnetic field. An advancer can automatically advance the medical device when the guide member is in the proper orientation.

Thus, the guide 20 can be used to deploy any type of medical device in the body, including catheters and cannulas, endoscopes, laser devices, RF devices, cryo devices, drug needles, biopsy tools, physiological sensors, deep brain stimulators, or other diagnostic and therapeutic devices. The guide 20 can also be used to orient various types of imaging and sensing equipment for example digital cameras, infrared sensors, and ultrasonic sensors.

A first alternate construction of the guide, indicated generally as 20', is shown in FIG. 8. The guide 20' is similar in construction guide 20, and corresponding parts are identified with corresponding reference numerals, except that in guide 20' the guide member 30' is made of a composite of permeable magnetic material and permanent magnetic material. In particular the guide member 30' comprises a tube 42 of a permanent magnetic material, and a generally spherical body 44 of permeable magnetic material.

Figure 9:
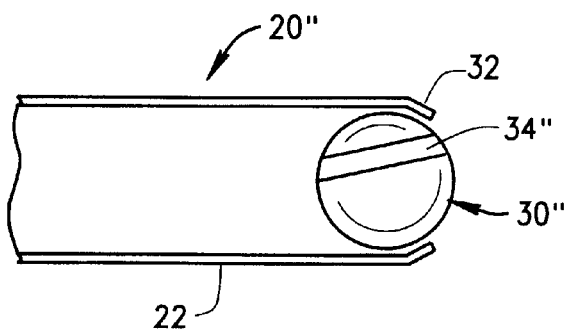
FIG. 9 is a longitudinal cross sectional view of an alternate construction of the guide of the first embodiment, in which the guide passage is off center.

A second alternate construction of the guide, indicated generally as 20", is shown in FIG. 9. The guide 20" is similar in construction guide 20, and corresponding parts are identified with corresponding reference numerals, except that in guide 20" the passage 34" in the guide member 30" does not extend diametrically through guide member. This allows the proximal end of the passage to remain generally in the center of the lumen 28, facilitating the passage of medical devices 40. The medical device can still be deployed in any orientation by a combination of a relatively small movement of the guide member 30" together with a rotation of the guide member generally about the axis of the cannula 22.

Figure 10:
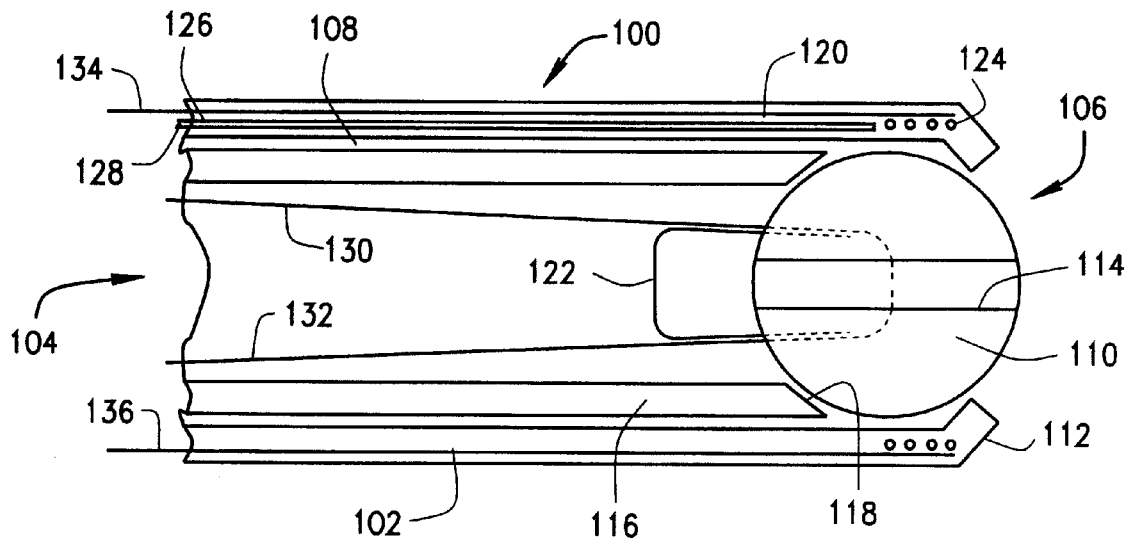
FIG. 10 is an enlarged longitudinal cross-sectional view of a second embodiment of a guide constructed according to the principles of this invention.

As shown in FIGS. 6 and 7, the medical device 40 can have one or more magnetically responsive elements, such as magnets 42 adjacent its distal end, so that after it is deployed is the desired initial direction, the distal end can be navigated with the assistance of the externally applied magnetic field. The magnets 42 can be any permanent magnet material, such as a Neodymium-Iron-Boron (Nd—Fe—B) compound. Alternatively, instead of a permanent magnetic material, the magnet 42 could be a permeable magnetic material. A second embodiment of a guide constructed according to the principles of this invention is indicated generally as 100 in FIG. 10. The guide 100 comprises a cannula 102, having a proximal end 104, and a distal end 106, and a lumen 108 therethrough. The cannula 102 is preferably fairly stiff or rigid, made from any suitable material, such as a non-magnetic stainless steel. There is a guide member 110 in the cannula 102, mounted for movement in response to an applied magnetic field. In the first preferred embodiment shown in FIG. 10, the distal end 106 has a lip 112 for retaining the guide member 110 in the cannula. The guide member 110 has a passage 114 therethrough for orienting or guiding a magnetic medical device.

The guide member 110 is preferably generally spherical, and the passage 114 extends generally diametrically through the sphere. The guide member 110 is preferably made of a magnetic material so that the guide member moves in response to an externally applied magnetic field. This magnetic material may either be a permeable magnetic material, or preferably a permanent magnetic material. A permanent magnetic material allows the guide member to have a permanent magnetic orientation so that when a magnetic field is applied, the direction of the guide member is precisely controlled. When a permeable magnetic material is used, the orientation of the guide member can be ambiguous, and to prevent the guide member from assuming an undesirable orientation, stops (not shown) may be provided on the guide member.

The guide 100 preferably further comprises a lock for selectively locking the guide member 110 in a selected orientation. In this preferred embodiment, the lock is a sleeve 116, with a beveled distal end 118 for engaging the guide member, that can be advanced distally to engage and lock the guide member 110, and retracted distally to release the guide member to allow it to move in response to an applied magnetic field. The sleeve 116 is preferably biased with a spring, which mediates the force applied on the guide member preventing deformation of the guide member, and reducing the risk that the guide member will be pushed from the distal end of the guide.

The guide 100 further comprises three coils 120, 122, and 124 mounted on, or formed in the sidewall of the cannula 102. Coils 120 is oriented generally axially, and has leads 126 and 128 for selectively powering the coil. Coil 122 is also oriented generally axially, but is offset 90' from coil 120, so that the coils are in effect in mutually perpendicular planes. Leads 130 and 132 extend from the coil 122 for selectively powering the coil. Coil 124 is oriented circumferentially around the wall of the cannula 102, so that coil 124 is in a plane generally perpendicular to coils 120 and 122, and thus all three coils are in mutually perpendicular planes. Leads 134 and 136 extend from coil 124 for selectively powering the coil. The three coils 120, 122, and 124 can be selectively powered to create a local magnetic field in virtually any direction to orient the guide member 110. Thus the guide member 110 can be selectively oriented, by controlling power to the coils, and when the guide member is in the desired position, a medical device can be advanced through the lumen of the cannula, and through the passage 114 in the desired direction.

The coils can alternatively or additionally be used to sense the orientation of the guide member, in order to confirm the direction in which a medical device will exit the guide 100.

A third embodiment of a guide for a medical device constructed according to the principles of this invention is indicated generally as 200 in FIGS. 11 through 14. The guide 200 comprises a cannula 202, having a proximal end 204, and a distal end 206, and a lumen 208 therethrough. The cannula 202 is preferably fairly stiff or rigid, made from any suitable material such as a non-magnetic stainless steel. There is a guide member 210 in the cannula 202, mounted for movement in response to an applied magnetic field. In the first preferred embodiment shown in the Figures, the distal end 206 has a lip 212 for retaining the guide member 210 in the cannula. The guide member 210 has a passage 214 therethrough for orienting or guiding a magnetic medical device.

The guide member 210 is preferably generally spherical, and the passage extends generally diametrically through the sphere.

The guide 200 preferably further comprises a lock for selectively locking the guide member 30 in a selected orientation. In this preferred embodiment the lock is a sleeve 216, with a beveled distal end 218 for engaging the guide member, that can be advanced distally to engage and lock the guide member 210, and retracted distally to release the guide member to allow it to move in response to an applied magnetic field. The sleeve 216 is preferably biased with a spring, which mediates the force applied on the guide member preventing deformation of the guide member, and reducing the risk that the guide member will be pushed from the distal end of the guide.

Figure 11:
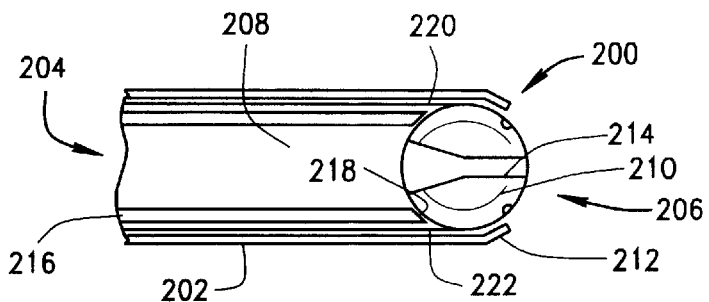
FIG. 11 is a longitudinal cross-sectional view of a third embodiment of a guide constructed according to the principles of this invention.
Figure 12:
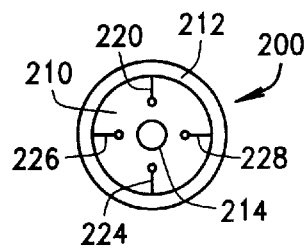
FIG. 12 is an end elevation view of the guide of the third embodiment.

The guide 200 further comprises some apparatus for mechanically or hydraulically changing the direction of the guide member 210, for example a plurality of pull wires for mechanically changing the orientation of the guide member. In the preferred embodiment there are four pull wires 220, 222, 224, and 226, attached to the guide member 210, and extending to the proximal end of the guide 200. The four pull wires are preferably arranged in opposing pairs 220, 222 and 224, 226, with each pair 90° apart. The four pull wires 220, 220, 224, and 226 can be selectively pulled to change the orientation of the guide member, and thus the orientation of the passage 214, so that when a medical device is fed through the lumen 208 of the cannula 202 and through the passage 214, it exits the guide in the selected direction. As shown in FIGS. 11 and 12, the magnetic member 210 is in a neutral position. By operating the guide wire 220, the magnetic member 210 changes orientation, to deliver a medical device in a different direction.

Figure 13:
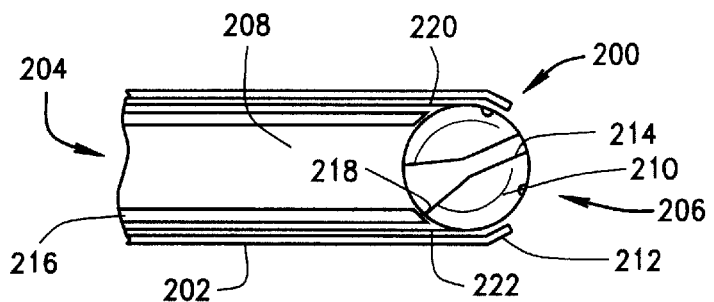
FIG. 13 is a longitudinal cross sectional view of the guide of the third embodiment with the guide member moved from its position in FIG. 11.
Figure 14:
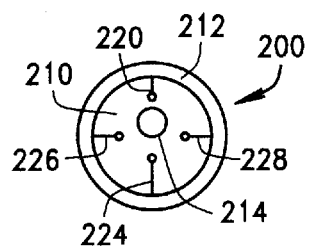
FIG. 14 is an end elevation view of the guide of the third embodiment.
Figure 15:
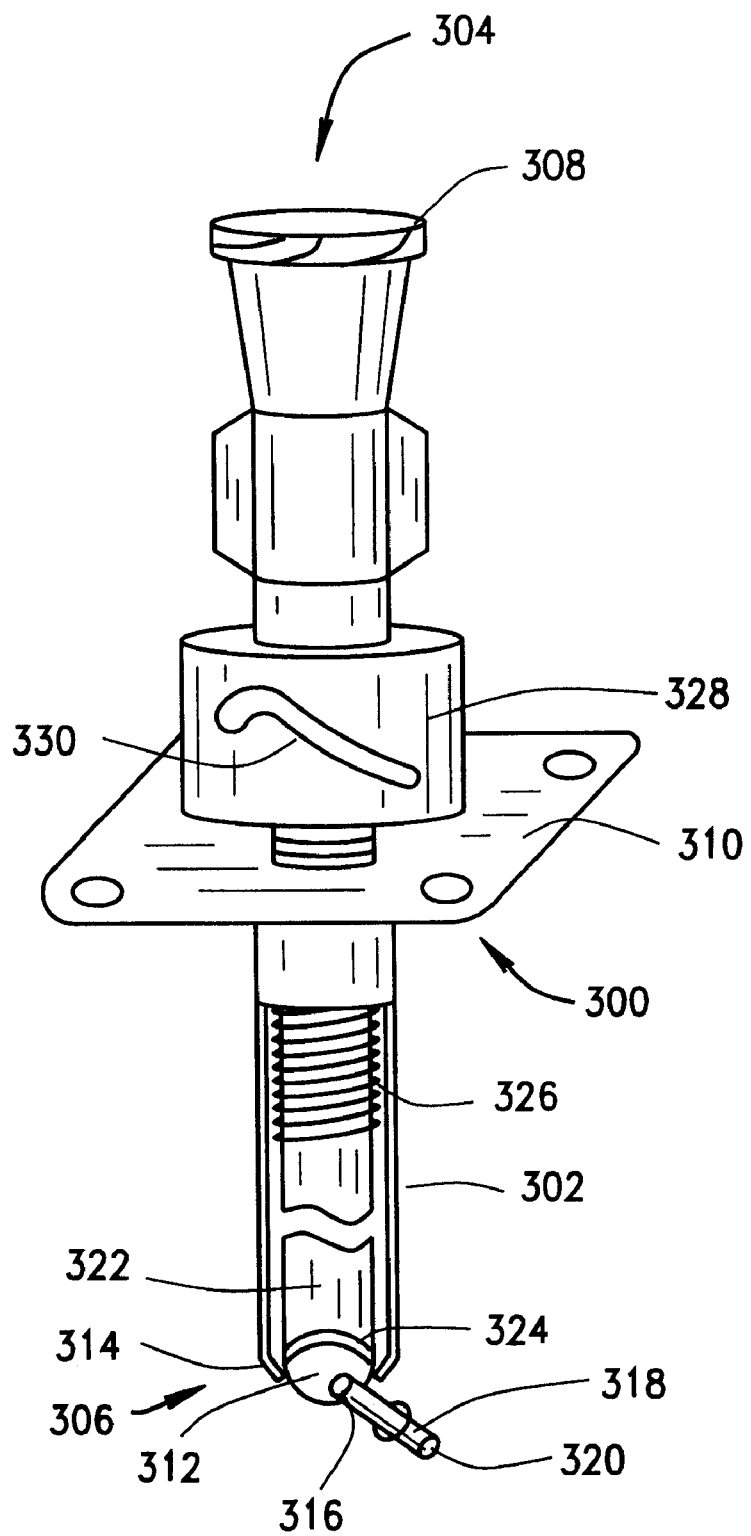
FIG. 15 is perspective view of a fourth embodiment of a guide constructed according to the principles of this invention, with portions broken away to review details of construction.
Figure 16:
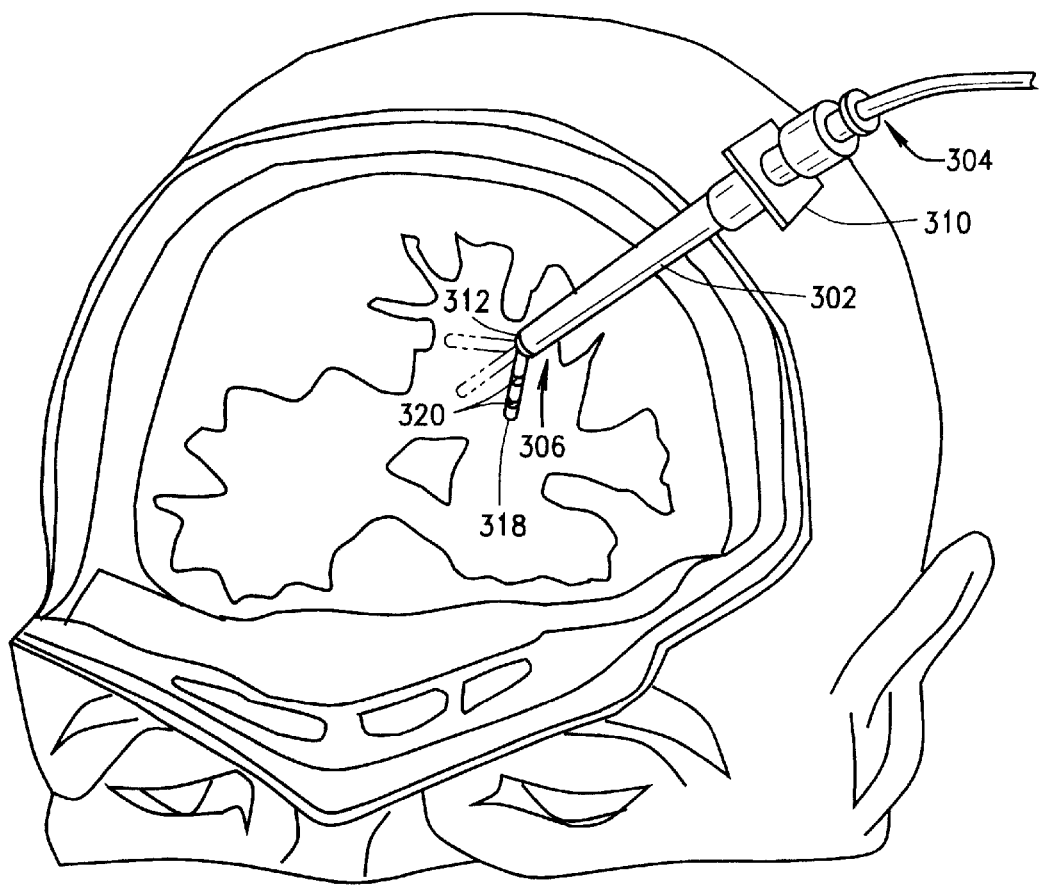
FIG. 16 is a perspective view of the guide of the fourth embodiment, as it would be used to delivery a deep brain stimulator.

A fourth embodiment of a guide constructed according to the principles of this invention is indicated generally as 300 in FIG. 13. The guide 300 comprises a cannula 302, having a proximal end 304, and a distal end 306, and a lumen 308 therethrough. The guide 300 further comprises a plate 310, intermediate the proximal and distal ends by which the guide can be secured to the skull of a patient. The cannula is threadedly connected to the plate so that the cannula can be threaded into and out of the patient's brain. The cannula 302 is preferably fairly stiff or rigid, made from any suitable material, such as a non-magnetic stainless steel. There is a guide member 312 at the end of the cannula 302, mounted for movement in response to an applied magnetic field. In the first preferred embodiment shown in the Figures, the distal end 306 has a lip 314 for retaining the guide member 312 in the cannula. The guide member 312 has a passage 316 therethrough for orienting or guiding a magnetic medical device, such as the electrode 318 of a deep brain stimulator.

The guide member 312 is preferably generally spherical and the passage extends generally diametrically through the sphere. The guide member 312 is preferably made of a magnetic material so that the guide member moves in response to an externally applied magnetic field. This magnetic material may either be a permeable magnetic material, or preferably a permanent magnetic material. A permanent magnetic material allows the guide member to have a permanent magnetic orientation so that when a magnetic field is applied, the direction of the guide member is precisely controlled. When a permeable magnetic material is used, the orientation of the guide member can be ambiguous, and to prevent the guide member from assuming an undesirable orientation, stops (not shown) may be provided on the guide member.

The guide 300 preferably further comprises a lock for selectively locking the guide member 300 in a selected orientation. In this preferred embodiment, the lock is a sleeve 322 inside the cannula, with a beveled distal end 324 for engaging the guide member, that can be advanced distally to engage and lock the guide member 312, and retracted distally to release the guide member to allow it to move in response to an applied magnetic field. The sleeve 322 is preferably biased with a spring 326, which mediates the force applied on the guide member preventing deformation of the guide member, and reducing the risk that the guide member will be pushed from the distal end of the guide. A collar 328, with a lock 330, is provided on the cannula 302 for securing the sleeve 322 in position against the guide member 312.

A burr hole is made in the skull, and the distal end 306 of the cannula is inserted through the hole and into the brain. The plate 310 is secured to the skull. The guide member 312 is oriented in the appropriate direction so that the passage 314 is aligned with the desired direction of deployment of the electrode. Once the proper orientation of the guide member 312 is achieved, the guide member 312 is locked by urging collar 328 downwardly, to urge sleeve 322, via spring 326, down against the guide member 312. The spring 326 helps to prevent the sleeve from damaging the guide member 312, or expelling it from the distal end 306 of the cannula 302.

Figure 17:
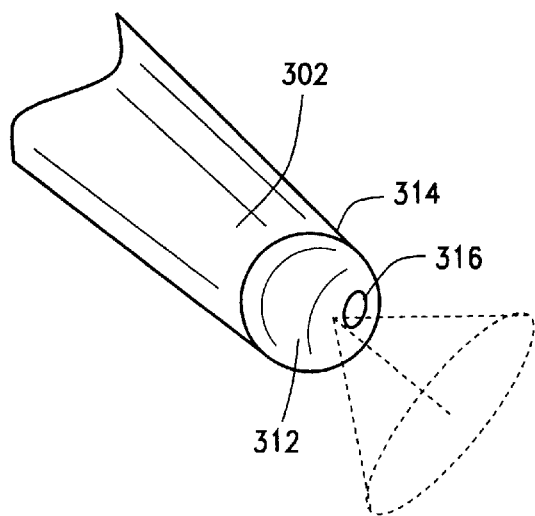
FIG. 17 is a perspective view of the distal end of the guide of the fourth embodiment.

A deep brain stimulator is advanced through the lumen 308 of the cannula 302, to the guide member 312. The electrode passes out the passage 316 in the direction of the passage. The electrode 318, preferably has a magnet 320 adjacent its distal end so that after the guide member 312 is locked, the distal end of the electrode can be navigated to its desired location by the application of an external magnetic field. By automating the control of the external magnetic field, and the advancement of the electrode, the placement of the electrode can be automated. This is particularly true where through localization (e.g., electromagnetic localization) or visualization (e.g., biplanar fluoroscopy), the exact position of the electrode ran be determined, so that feed back can be provided to the automated navigation process. The user can simply identify the desired end point on two screens of a bi-planer fluoroscopic imaging system, or the user can identify the desired end point on a pre-procedure image, such as an MRI. Through computer control, the distal end of the electrode can be brought to the selected location. FIG. 17 shows a cone containing the possible orientations that can be achieved with by the guide.

Figure 18:
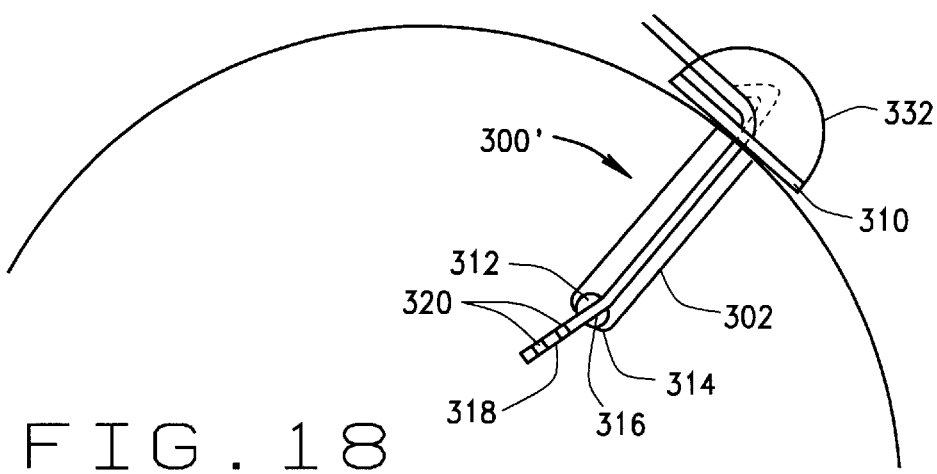
FIG. 18 is side elevation view of an alternate construction of the guide of the fourth embodiment.

An alternative construction of the guide of the fourth embodiment, indicated generally as 300' in FIG. 18, is shown as it would be positioned though the skull of the patient. Guide 300' is similar in construction to guide 300, and corresponding parts are identified with corresponding reference numerals. However, unlike guide 300, guide 300' has a dome 332, into which the deep brain stimulator can be withdrawn (as shown in dashed lines) while the guide member is being re-oriented. This allows the guide to be left in place and used to move or place an additional deep brain stem in the head of a patient.

Figure 21:
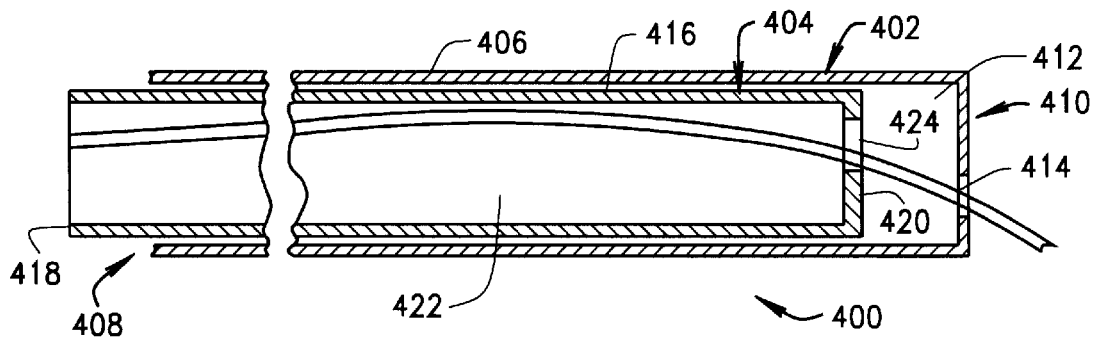
FIG. 21 is a longitudinal cross-sectional view of the fifth embodiment of redirection device, after the device has been mechanically operated to guide a catheter in a different direction than shown in FIG. 19.
Figure 22:
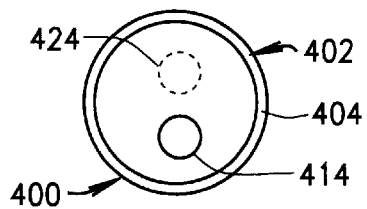
FIG. 22 is a distal end elevation view of the redirection device of the fifth embodiment, shown in its position in FIG. 21.
Figure 19:
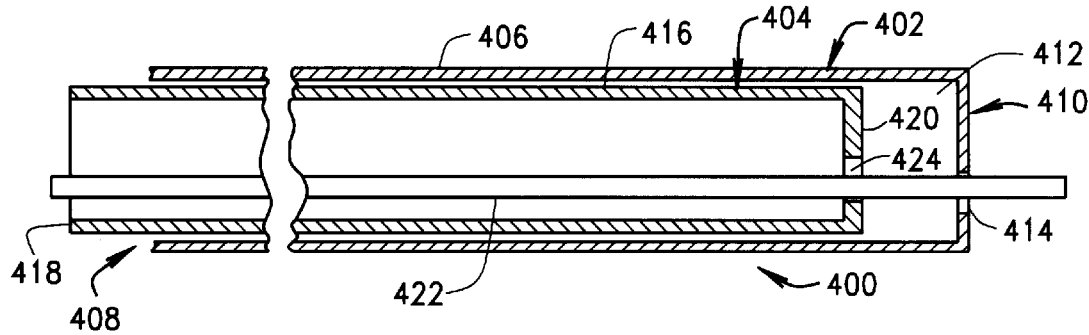
FIG. 19 is a longitudinal cross-sectional view of fifth embodiment of a redirection device constructed according to the principles of this invention.
Figure 20:
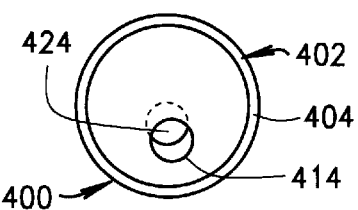
FIG. 20 is a distal end elevation view of the redirection device of the fifth embodiment, shown in its position in FIG. 19.

A fifth embodiment of a redirection device constructed according to the principles of this invention is indicated generally as 300 in FIGS. 19–22. As shown in FIGS. 19 and 21, the redirection device 400 comprises an outer section 402 and an inner section 404. The outer section 402 is generally tube-shaped, comprising a sidewall 406, having a proximal end 408, a distal end 410, and a lumen 412 therebetween. The distal end 410 is substantially closed, having a passage 414 therein. The passage 414 is preferably eccentrically positioned in the closed end 410 (i.e., it is preferably not located at the center of the end). The inner section 404 is of similar construction to the outer section 402, and is generally tube-shaped, comprising a sidewall 416, having a proximal end 418, a distal end 420, and a lumen 422 therebetween. The distal end 420 is substantially closed, having a passage 424 therein. The passage 424 is preferably eccentrically positioned in the closed end 420 (i.e., it is preferably not located at the center of the end).

The outer section 402 and the inner section 404 are relatively rotatable, i.e., the inner section 404 can rotate relative to the outer section 402. If at least one of the passages 414 in the outer section and 424 in the inner section is eccentric, the relative rotation of the outer and inner sections causes a medical device, such as a catheter, that extends through the two passages to change direction. Thus, as shown in FIG. 19, when the outer and inner sections 402 and 404 are positioned so that their passages 414 and 424 are aligned, a catheter extending through the redirection device 400 extends from the device generally parallel to the axis of the distal end portion. However, as shown in FIG. 21, when the outer and inner sections 402 and 404 are rotated relative to each other, such that their passages 414 and 424 are not aligned, a catheter extending through the redirection device, extends from the device at an angle determined by the relative positions of the outer and inner sections 402 and 404. By controlling the relative positions by rotating the outer and/or inner sections, the physician can direct a catheter or other medical device in selected directions.

Figure 23:
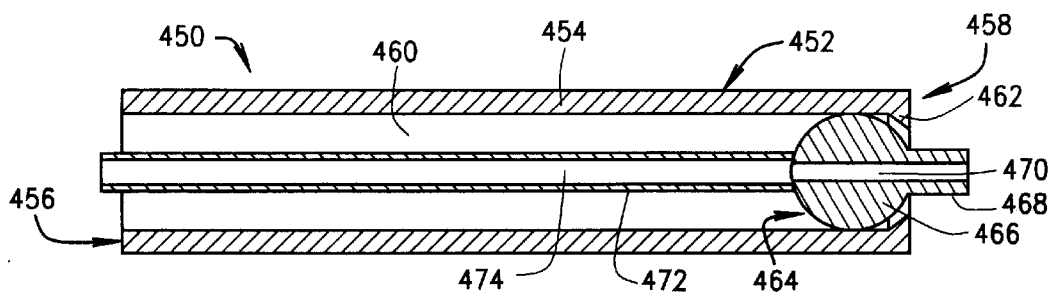
FIG. 23 is a longitudinal cross-sectional view of a sixth embodiment of a redirection device constructed according to the principles of this invention.
Figure 24:
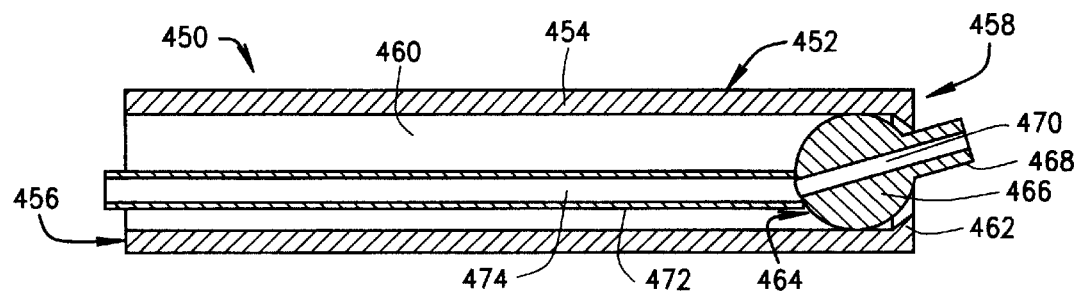
FIG. 24 is a longitudinal cross-sectional view of the sixth embodiment of the redirection device constructed according to the principles of this invention, after the guide has been magnetically reoriented from the position shown in FIG. 23.

A sixth embodiment of a redirection device constructed according to the principles of this invention is indicated generally as 450 in FIGS. 23 and 24. As shown in FIGS. 23 and 24, the redirection device 450 comprises a cannula 452, having a sidewall 454 with a proximal end 456 and a distal end 458, and a lumen 460 therebetween. There is a preferably a stricture 462 at the distal end 458 retaining a guide member therein. This stricture 462 can be formed integrally in the distal end of the sidewall 454, or it can be a separate piece secured on the distal end of the cannula 452. A guide member 464 is disposed in the lumen 460 of the cannula 452, adjacent the distal end 458. The guide member 464 includes a spherical body 466, having a magnetic tube 468 mounted thereon. The spherical body 466 may be but need not be made of a magnetically responsive material (i.e., a permanent magnetic material, or a permeable magnetic material), but the magnetic tube 468 is made of a magnetically responsive material, either a permanent magnetic material, such as Nd—Fe—B, or a permeable magnetic material. A passage 470 extends through the spherical body 466 and the magnetic tube 468. A flexible sheath 472, having a lumen 474 therethrough, extends proximally from the passage 470. The sheath 472 may incorporate a coil or braid to prevent kinking. An elongate magnetic medical device can be advanced through the lumen 474 of the sheath 472, into the passage 470 through the spherical body 466 and the magnetic tube 468. The orientation of the magnetic tube 469, and thus the direction that the medical device leaves the redirection device 450 can be controlled by applying a magnetic field with an external magnet system, which may include one or more electromagnets and/or permanent magnets. An interface can be provided to allow the physician to select the direction in which to direct the medical device, and operate the external magnetic system to apply the appropriate magnetic field to orient the magnetic tube in the correct direction. The device can then be advanced in the selected direction. A lock mechanism, as described above, can be provided to secure the guide member 464 in a selected position.

The guide 450 can be used in automatically deploying devices. An interface can receive the physician's input on a direction and/or destination, control the external magnet system to orient the guide in the proper direction, and control an advancer to automatically advance the medical device through the guide in the proper direction, for the proper distance.

Figure 25:
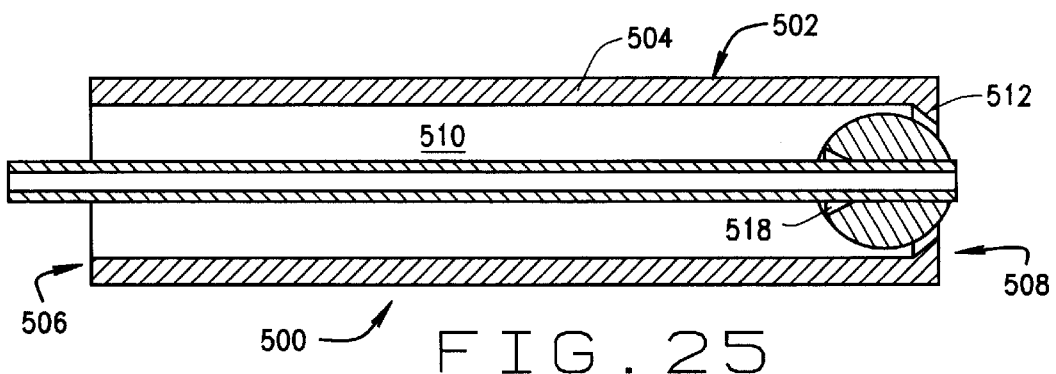
FIG. 25 is a longitudinal cross-sectional view of a seventh embodiment of the redirection device constructed according to the principles of this invention.
Figure 26:
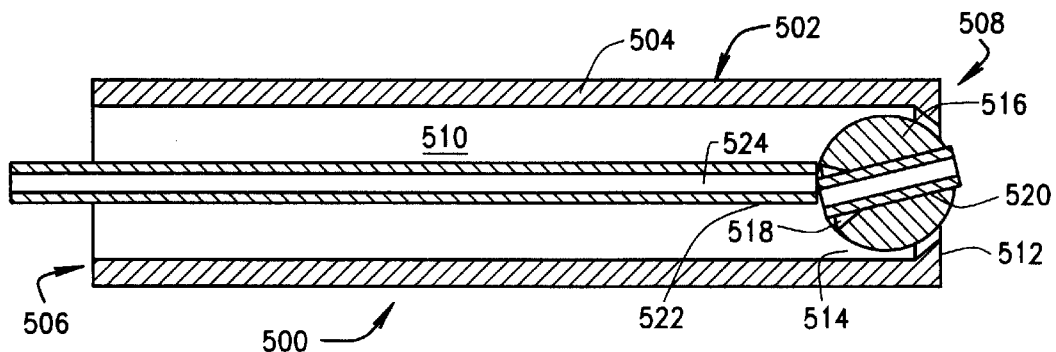
FIG. 26 is a longitudinal cross-sectional view of the redirection device of the seventh embodiment, after the guide has been magnetically reoriented from the position shown in FIG. 25.
Figure 27:
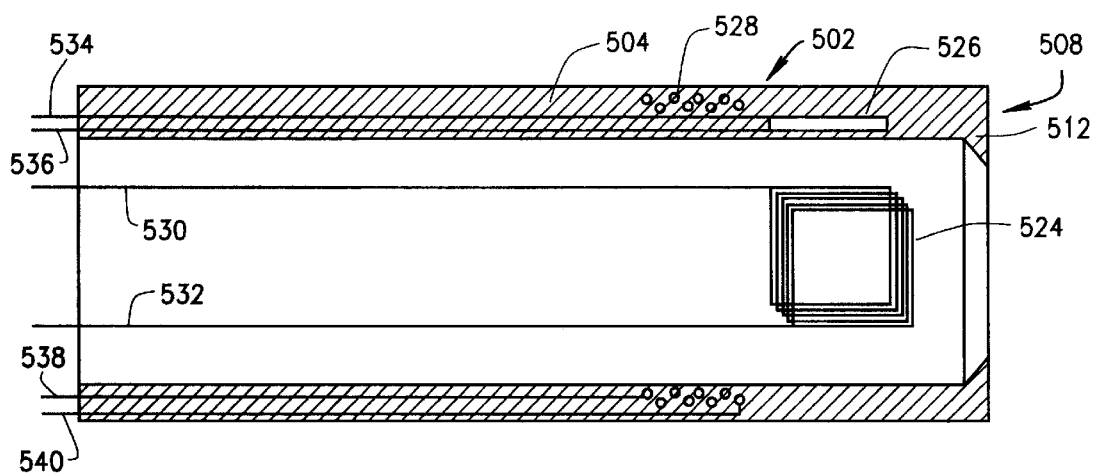
FIG. 27 is an enlarged longitudinal cross sectional view of the redirection device of the seventh embodiment, with the guide removed, to show the coils embedded in the distal end of the device for magnetically moving the guide.
Figure 28:
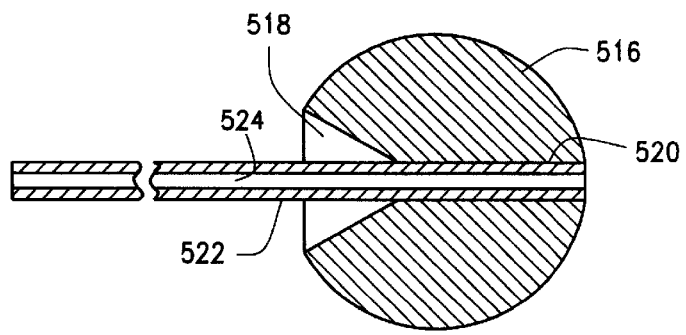
FIG. 28 is an enlarged longitudinal cross-sectional view of the guide member of the redirection device of the seventh embodiment.

A seventh embodiment of a redirection device is indicated generally as 500 in FIGS. 25–28. As shown in FIGS. 25 and 26, the redirection device 500 comprises a cannula 502, having a sidewall 504 with a proximal end 506 and a distal end 508, and a lumen 510 therebetween. There is a preferably a stricture 512 at the distal end 508 retaining a guide member therein. This stricture 512 can be formed integrally in the distal end of the sidewall 504, or it can be a separate piece secured on the distal end of the cannula 502. A guide member 514 is disposed in the lumen 510 of the cannula 502, adjacent the distal end 508. As shown in FIG. 28, the guide member 514 includes a spherical body 516. The spherical body 516 is made from, or includes, a magnetically responsive material. In particular it may be made from or include a permanent magnetic material, such as Nd—Fe—B, or a permeable magnetic material. A passage 520 extends through the spherical body 516. A flexible sheath 522, having a lumen 524 therethrough, extends proximally from the passage 520. The sheath 522 may incorporate a coil or braid to prevent kinking. There may be a conical cut out 518 in the spherical body 516 to accommodate the sheath 522 as the spherical body moves to guide a medical device, as described below. An elongate magnetic medical device can be advanced through the lumen 524 of the sheath 522, into the passage 520 through the spherical body 516. The orientation of the spherical body 516, and thus the direction that the medical device leaves the redirection device 500 can be controlled by applying a magnetic field to the spherical body. In this seventh preferred embodiment this is accomplished with three magnetic coils incorporated into the cannula 502.

As shown in FIG. 27, three coils 524, 526, and 528 are embedded in the wall of the cannula 502. Coil 524 is arranged in a plane parallel to the longitudinal axis of the cannula, and has leads 530 and 532 extending therefrom so that the coil can be selectively connected to a power source to create a magnetic field. Coil 526 is arranged in a plane parallel to the longitudinal axis of the cannula, and perpendicular to the plane of coil 524, and has leads 534 and 536 extending therefrom so that the coil can be selectively connected to a power source to create a magnetic field. Coil 528 is arranged in a plane perpendicular to the longitudinal axis of the cannula, and has leads 538 and 540 extended therefrom so that the coil can be selectively connected to a power source to create a magnetic field. By selectively connecting the coils 524, 526, and 528 to a power source, a magnetic field can be created in the vicinity of the spherical body 516 to orient the body in a selected direction.

Of course fewer coils could be provided, or coils in some other arrangement could be provided. The range of motion of the spherical body 516 is limited, so it may not be necessary to be able to provide a magnetic field in any direction, as is possible with the three mutually orthogonal coils 524, 526, and 528.

An interface can be provided to allow the physician to select the direction in which to direct the medical device, and energize the coils 524, 526, and 528 to apply the appropriate magnetic field to orient the spherical body 516 in the correct direction. The device can then be advanced in the selected direction. A lock mechanism, as described above, can be provided to secure the guide in a position.

The guide 500 can be used in automatically deploying medical devices. An interface can receive the physician's input on a direction and/or destination, control the coils 524, 526, and 528 to orient the guide in the proper direction, and control an advancer to automatically advance the medical device through the guide in the proper direction, for the proper distance.

Figure 29:
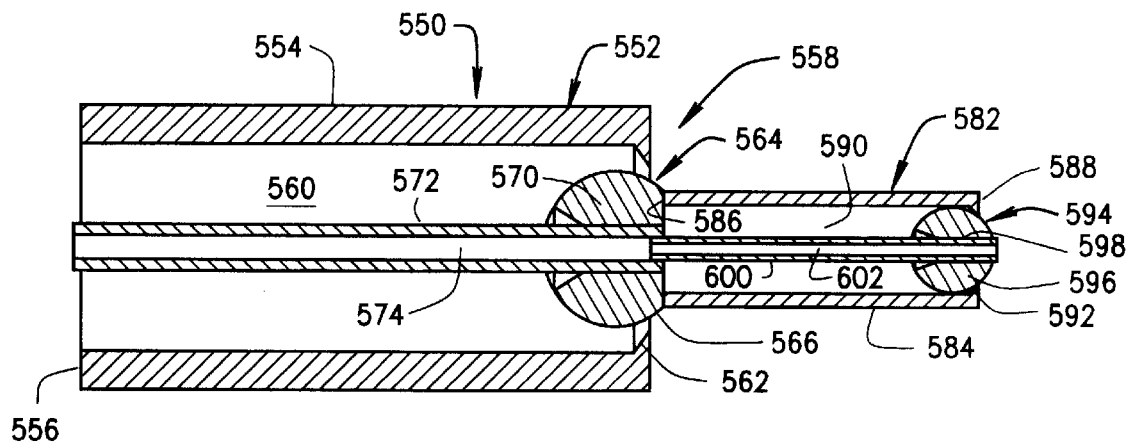
FIG. 29 is a longitudinal cross-sectional view of an eight embodiment of the redirection device constructed according to the principles of this invention.
Figure 30:
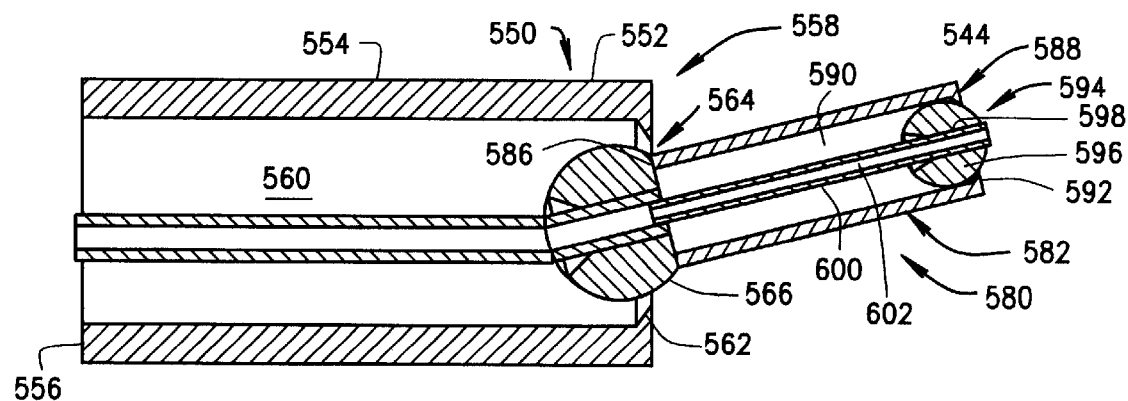
FIG. 30 is a longitudinal cross-sectional view of the redirection device of the eight embodiment, after the guide has been magnetically reoriented from the position shown in FIG. 29.

An eighth embodiment of a redirection device constructed according to the principles of this invention is indicated generally as 550 in FIGS. 29 and 30. As shown in FIGS. 29 and 30, the redirection device 550 comprises a cannula 552, having a sidewall 554 with a proximal end 556 and a distal end 558, and a lumen 560 therebetween. There is a preferably a stricture 562 at the distal end 568 retaining a guide member therein. This stricture 562 can be formed integrally in the distal end of the sidewall 554, or it can be a separate piece secured on the distal end of the cannula 552. A guide member 564 is disposed in the lumen 560 of the cannula 562, adjacent the distal end 568. The guide member 564 includes a spherical body 566. The spherical body 566 is made from, or includes, a magnetically responsive material. In particular it may be made from or include a permanent magnetic material, such as Nd—Fe—B, or a permeable magnetic material. A passage 570 extends through the spherical body 566. A flexible sheath 572, having a lumen 574 therethrough, extends proximally from the passage 520. The sheath 572 may incorporate a coil or braid to prevent kinking. There may be a conical cut out in the conical body 566 to accommodate the sheath 572 as the spherical body moves to guide a medical device, as described below.

As shown in FIGS. 29 and 30 an extension 580 comprises a cannula 582, having a sidewall 582 with a proximal end 586 and a distal end 588, and a lumen 590 therebetween. The proximal end 584 is secured to the spherical body 566. There is a preferably a stricture 592 at the distal end 558 retaining a guide member therein. This stricture 592 can be formed integrally in the distal end of the sidewall 582, or it can be a separate piece secured on the distal end of the cannula 582. A guide member 594 is disposed in the lumen 590 of the cannula 582, adjacent the distal end 588. The guide member 594 includes a spherical body 596. The spherical body 596 is made from, or includes, a magnetically responsive material. In particular it may be made from or include a permanent magnetic material, such as Nd—Fe—B, or a permeable magnetic material. A passage 598 extends through the spherical body 596. A flexible sheath 600, having a lumen 602 therethrough, extends proximally from the passage 598. The sheath 600 may incorporate a coil or braid to prevent kinking. There may be a conical cut out in the spherical body 596 to accommodate the sheath 600 as the spherical body moves to guide a medical device, as described below.

The redirection is thus articulated, such that the orientation of the extension 580 relative to the cannula 552 can be adjusted, and the orientation of a medical device leaving the distal end of the cannula 582 can be adjusted. The orientation of the extension 580 relative to the cannula 552 is adjusted by moving the spherical body 566, and the orientation of the medical device relative to the cannula 582 is adjusted by moving the spherical body 596. The spherical bodies 566 and 596 are magnetically responsive and can be moved by the application of a magnetic field. This application of a magnetic field can be accomplished with a magnet system comprising one or more electromagnets and/or permanent magnets. Preferably, however, this is accomplished with one or more electromagnetic coils in the cannulas 552 and 582. Coils (like the coils 524, 525, and 528 in device 500) can be provided in the distal end of cannula 552, to selectively apply a magnetic field to orient the spherical body 566 is a desired direction. Similarly, coils (like the coils 524, 525, and 528 in device 500) can be provided in the distal end of cannula 582, to selectively apply a magnetic field to orient the spherical body 596 is a desired direction.

More specifically, three coils are embedded in the wall of the cannula 552. A first coil is arranged in a plane parallel to the longitudinal axis of the cannula, and has leads extending therefrom so that the coil can be selectively connected to a power source to create a magnetic field. A second coil is arranged in a plane parallel to the longitudinal axis of the cannula, and perpendicular to the plane of the first coil, and has leads extending therefrom so that the coil can be selectively connected to a power source to create a magnetic field. A third coil is arranged in a plane perpendicular to the longitudinal axis of the cannula, and has leads extending therefrom so that the coil can be selectively connected to a power source to create a magnetic field. By selectively connecting the coils to a power source, a magnetic field can be created in the vicinity of the spherical body 556 to orient the body in a selected direction. Similarly, Three coils are embedded in the wall of the cannula 582. A first coil is arranged in a plane parallel to the longitudinal axis of the cannula, and has leads extending therefrom so that the coil can be selectively connected to a power source to create a magnetic field. A second coil is arranged in a plane parallel to the longitudinal axis of the cannula, and perpendicular to the plane of the first coil, and has leads extending therefrom so that the coil can be selectively connected to a power source to create a magnetic field. A third coil is arranged in a plane perpendicular to the longitudinal axis of the cannula, and has leads extending therefrom so that the coil can be selectively connected to a power source to create a magnetic field. By selectively connecting the coils to a power source, a magnetic field can be created in the vicinity of the spherical body 596 to orient the body in a selected direction.

An interface can be provided to allow the physician to select the direction in which to orient the extension 580 and to select the direction to direct the medical device from the end of the extension 580, and energize the coils to apply the appropriate magnetic field to orient the spherical body 566 and extension 580, and to orient the spherical body 596, in the proper directions. A medical device can then be advanced through the device 550. Lock mechanisms can secure the guide members 564 and 594 in their selected orientations. The redirection device 550 can be used in automatically deploying devices. An interface can receive the physician's input on a direction and/or destination, control the coils to orient the guide member 564 and 594 in the proper directions, and control an advancer to automatically advance the medical device through the guide in the proper direction, for the proper distance.

Various radioopaque patterns can be incorporated into the guides, so that the position and/or orientation of the guide can be seen on x-ray or fluoroscopic images. Examples of these patters are shown in FIGS. 31A–31E.

Imaging can also be incorporated into redirection devices of the various embodiments of the present invention. As shown in FIG. 32, an optical fiber can be incorporated into a wall of a device, with the distal end positioned at the distal end of the device to provide an image from the distal end of the device useful in operating the redirection device. As shown in FIG. 33, an optical fiber can be incorporated into the medical device being deployed from the redirection device to provide an image from the direction in which the medical device is actually traveling. As shown in FIG. 34, multiple optical fibers can be incorporated into a wall of a device, with the distal ends positioned at the distal end of the device to provide an image from the distal end of the device useful in operating the redirection device. The multiple optical fibers allow for separate illumination and/or allow for stereoscopic imaging. As shown in FIG. 35, an optical fiber can be incorporated into the wall of the redirection device such that it projects from the distal end to a position more closely adjacent where the medical device exists the redirection device.

What is claimed is:

1. A magnetically operated guide for controlling the orientation of a medical device, the guide comprising:

a cannula having a lumen therein for the medical device;

a magnetic guide member having a passage therein for receiving and directing the medical device, the guide member being movably mounted in the cannula for movement in response to an applied magnetic field, to selectively change the orientation of the passage, and a medical device passing therethrough.

2. The magnetically operated guide according to claim 1 wherein the magnetic guide member is generally spherical.

3. The magnetically operated guide according to claim 1 wherein the magnetic guide member is a permeable magnetic material.

4. The magnetically operated guide according to claim 1 wherein the magnetic guide member is a permanent magnetic material.

5. The magnetically operated guide according to claim 1 wherein the magnetic guide member is a composite of permanent magnetic material and permeable magnetic material.

6. The magnetically operated guide according to claim 1 wherein the cannula has a proximal end and a distal end, and wherein the guide member is located generally adjacent the distal end.

7. The magnetically operated guide according to claim 1 wherein the cannula has a proximal end and a distal end, and wherein the guide member is located intermediate the proximal end and the distal end.

8. In combination with an elongate magnetic medical device, a guide for controlling the orientation of a medical device, the guide comprising:

cannula having a lumen therein through which the medical device extends;

a guide member having a passage therein for receiving and directing an magnetic device, the guide being movably mounted in the cannula to move in response to a magnetic field applied to the magnetic medical device in the passage, to selective change the orientation of the passage, and a medical device passing therethrough.

9. A guide for controlling the orientation of a medical device, the guide comprising: a cannula having a lumen therein for the medical device; a guide member having a passage therein for receiving and directing the medical device, the guide member being movably mounted in the cannula for movement; and a mechanism for selectively moving the guide member to selectively change the orientation of the passage, and a medical device passing therethrough.

10. A guide for controlling the orientation of medical device, the guide comprising: a cannula having a lumen therein for the medical device; a guide member having a passage therein for receiving and directing the medical device, the guide member having a passage therein for receiving and directing the medical device, the guide member being movably mounted in the cannula for movement; and means for selectively moving the guide member to selectively change the orientation of the passage.

11. A method of reorienting a medical device in the body, the method comprising:

introducing a guide member at least partially into the subject's body, the guide member comprising a cannula having a lumen therein for the medical device, and a guide member having a passage therein for receiving and directing the medical device, the guide member being movably mounted in the cannula for movement in response to an applied magnetic field, to selectively change the orientation of the passage, and a medical device passing therethrough, so that the guide member is disposed inside the subject's body;

moving the guide member inside the subject's body to reorient the passage and thus the medical device extending therethrough.

12. The method according to claim 11 wherein the guide member is magnetically responsive, and wherein the step of moving the guide member comprises applying magnetic field to the guide member to move the guide member.

13. The method according to claim 12 wherein the magnetic field is applied to the guide member from a source magnet outside the patient's body.

14. The method according to claim 12 wherein the guide includes at least one electromagnetic coil, and wherein the magnetic field is applied to the guide member from the at least one electromagnetic coil.

15. The method according to claim 11 wherein the guide includes a mechanism for remotely moving the guide member, and wherein the step of moving the guide member comprises operating the mechanism to move the guide member.

16. The guide according to claim 1 further comprising at least one electromagnetic coil that can be selectively energized to move the magnetic guide member.

* * * * *